United States Patent [19]

Masuzawa et al.

[11] Patent Number: 4,753,953
[45] Date of Patent: Jun. 28, 1988

[54] PYRIDONECARBOXYLIC ACID DERIVATIVES AND ANTIBACTERIAL PHARMACEUTICAL COMPOSITIONS THEREOF

[75] Inventors: Kuniyoshi Masuzawa, Koga; Seigo Suzue; Keiji Hirai, both of Kuki; Takayoshi Ishizaki, Washimiya, all of Japan

[73] Assignee: Kyorin Pharmaceutical Co., Ltd., Tokyo, Japan

[21] Appl. No.: 876,420

[22] Filed: Jun. 20, 1986

[30] Foreign Application Priority Data

Jun. 28, 1985 [JP] Japan ................ 60-141813

[51] Int. Cl.$^4$ ............ A61K 31/47; C07D 215/56
[52] U.S. Cl. ................ 514/312; 514/230.2; 544/101; 546/156
[58] Field of Search ............ 544/101; 546/156; 514/234, 236, 233, 312

[56] References Cited

U.S. PATENT DOCUMENTS

| | | | |
|---|---|---|---|
| 4,292,317 | 9/1981 | Pesson | 546/156 X |
| 4,571,396 | 2/1986 | Hutt et al. | 544/101 X |
| 4,578,473 | 3/1986 | Domagala et al. | 546/156 |
| 4,604,401 | 8/1986 | Mich et al. | 546/156 X |
| 4,620,007 | 10/1986 | Grohe et al. | 546/156 |
| 4,665,079 | 5/1987 | Culbertson et al. | 546/156 X |

FOREIGN PATENT DOCUMENTS 88183 6/1982 Japan .
72589 4/1983 Japan .

Primary Examiner—Richard L. Raymond
Attorney, Agent, or Firm—Oblon, Fisher, Spivak, McClelland & Maier

[57] ABSTRACT

Pyridonecarboxylic acid derivatives of the following formula,

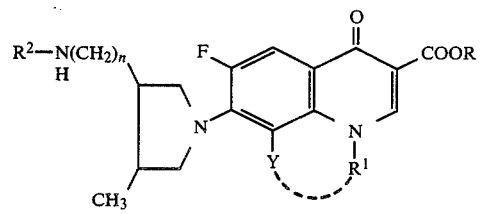

wherein R is hydrogen atom or lower alkyl group, $R^1$ is lower alkyl group, cycloalkyl group or haloalkyl group, Y is hydrogen atom or halogen atom, or Y and $R^1$ are

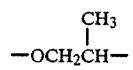

which work together, $R^2$ is hydrogen atom, lower alkyl group, alkoxycarbonyl group or acyl group and n is 0 or 1; the hydrates and pharmaceutically acceptable salts thereof are useful as antibacterial agents.

15 Claims, No Drawings

PYRIDONECARBOXYLIC ACID DERIVATIVES AND ANTIBACTERIAL PHARMACEUTICAL COMPOSITIONS THEREOF

DETAILED DESCRIPTION OF THE INVENTION

The present invention is concerned with certain novel useful pyridonecarboxylic acid derivatives of the formula (I), with a process for their preparation, and with compositions containing them.

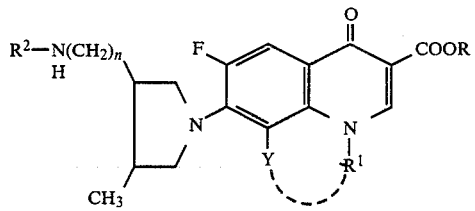

In formula (I), R is hydrogen atom or lower alkyl group, $R^1$ is lower alkyl group, cycloalkyl group, Y is hydrogen atom or halogen atom, or Y and $R^1$ are

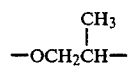

which work together, $R^2$ is hydrogen atom, lower alkyl group, alkoxycarbonyl group or acyl group and n is 0 or 1.

The term "lower alkyl group", as used herein, means alkyl radicals having from one to three carbon atoms such as methyl, ethyl and isopropyl.

The term "cycloalkyl group", as used herein, means cycloalkyl radicals having from three to five carbon atoms, as illustrated by cyclopropyl, cyclobutyl and cyclopentyl.

The term "halogen atom", as used herein, means fluorine, chlorine, bromine and iodine, especially, fluorine, chlorine and bromine.

The term "haloalkyl group", as used herein, means above-mentioned lower alkyl groups substituted by above-mentioned halogen atom, as illustrated by fluoroethyl, chloroethyl, difluoromethyl, and the like.

The term "alkoxycarbonyl group", as used herein, means lower alkoxycarbonyl radicals having from two to six carbon atoms, such as methoxy-, ethoxy-, t-butoxycarbonyl, and the like, or arylalkoxycarbonyl radicals such as benzyloxycarbonyl.

The term "acyl group", as used herein, means lower alkylcarbonyl radicals having from one to five carbon atoms or arylcarbonyl radicals or arylalkylcarbonyl radicals having from seven to twelve carbon atoms, as illustrated by formyl, acetyl, propionyl, benzoyl, and the like.

The compound represented by the formula (I), contains geometric isomers (cis and trans isomers) and their optical isomers, owing to the orientation of both substituents at the position 3 and 4 on the pyrrolidine ring, the 7-substituent. But all of the isomers and their mixture are represented, for convenience, by a unitary formula. Hence, the scope of the invention is not limited to one of the isomer or their mixture.

Since nalidixic acid which has been employed for treatment of urinary tract infections by gram-negative bacteria, was introduced in 1963, intensive work has been carried out on the further development of pyridonecarboxylic acid analogue.

Thus, recently a remarkable antibacterial activity against not only gram-negative bacteria but also gram-positive bacteria occurs for some compounds (e.g. norfloxacin). However their activity against gram-positive bacteria is fairly less than that against gram-negative bacteria.

Just recently, the drugs which have relatively strong activity against gram-positive bacteria (e.g. CI-934) has been developed, but shown to possess weaker activity against gram-negative bacteria than that of the prior compounds (e.g. norfloxacin, ciprofloxacin).

As a result of the investigation, the present inventors have now unexpectedly found that new derivatives of pyridonecarboxylic acid represented by the formula (I) have excitingly potential activity against gram-positive bacteria without decrease of activity against gram-negative bacteria in comparison with that of any prior analogue and therefore are superior to commercial preparations and investigational drugs in the in vitro and in vivo antibacterial activity against both gram-negative and gram-positive bacteria.

Furthermore, the compounds of this invention possess excellent antibacterial activity not only against aerobic bacteria but also against anaerobic bacteria.

The present compounds are well absorbed and distributed into the tissue when administered orally in animals.

The present compounds, therefore, are active at low doses against both gram-positive and gram-negative bacteria and thus constitute valuable agents for the treatment of infectious human, animal or plant diseases.

In the following, the process usable for the preparation of the compound of the invention is outlined.

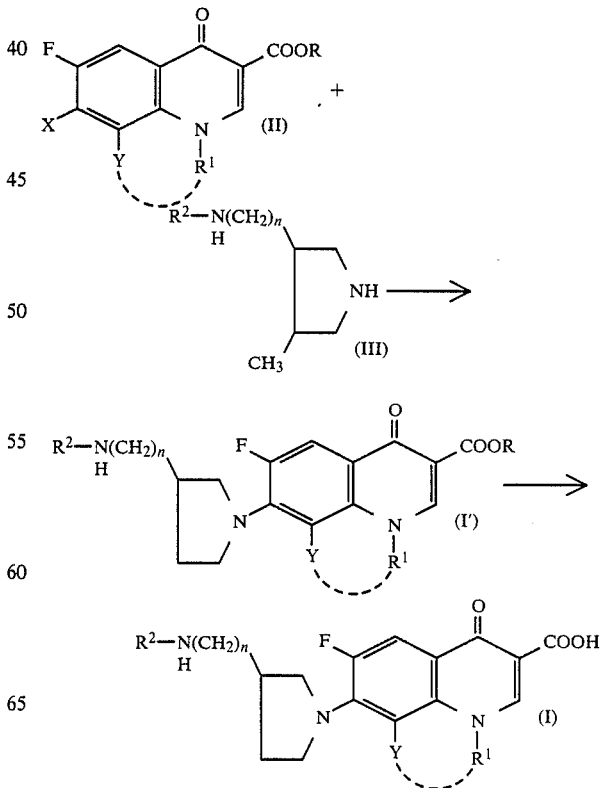

wherein R is hydrogen atom or lower alkyl group, R¹ is lower alkyl group, cycloalkyl group or haloalkyl group, Y is hydrogen atom or halogen atom, or Y and R¹ are

which work together, X is halogen atom, R² is hydrogen atom, lower alkyl group, alkoxycarbonyl group or acyl group and n is 0 or 1.

By allowing compounds represented by the formula (II) to react with amines presented by the formula (III), compound of this invention represented by the formula (I) is synthesized. However, in the case of compounds wherein R² is protecting group of an amino group in the formula (III), e.g., R² is alkoxycarbonyl group, for example, methoxy-, ethoxy-, t-butoxy-, benzyloxycarbonyl group and the acyl group, e.g., formyl, acetyl, propionyl, benzoyl group and the like, the resultants with the compounds represented by the formula (I') are removed the protecting group according to the usual method to give the compounds of this invention, wherein R² is hydrogen atom. Moreover, in the case of compounds wherein R is lower alkyl group in the formula (II), the reaction products obtained from the compounds represented by the formula (III) are hydrolyzed according to the usual method and ester is converted to carboxylic acid to offer the compound of the invention, wherein R is hydrogen atom. The reaction of compounds represented by the formula (III) preferably is carried out by heating the mixture in a solvent such as water, alcohols, acetonitrile, dimethylformamide (DMF), dimethyl sulfoxide (DMSO), hexamethylphosphoric triamide, pyridine, picoline and the like or in the absence of the solvent. The reaction temperature is selected appropriately in a range of room temperature to 200° C., preferably room temperature to 160° C. In more detail, it is preferable to allow compounds represented by the formula (II) to react with 1 to 5 times mole of compounds represented by the formula (III) for 1 to several hours at room temperature to 160° C. in 2 to 10 times volume of aforementioned solvents. At this time, the use of deacidifying agents such as triethylamine, diazabicyclo bases and potassium carbonate is also desirable. Moreover, compounds (I') wherein R is a lower alkyl group in the formula (I) can be hydrolyzed according to the usual method. Such hydrolysis can be carried out easily with alkalies such as potassium hydroxide or acids such as sulfuric acid at room temperature to boiling point of solvents in water, mixed liquor of water with alcohols, mixed liquor of water with acetic acid, and so on.

Furthermore, the compounds of the formula (I) can be converted, if desired, to the pharmaceutically acceptable ammonium salts or carboxylic acid metal salts by treatment with acid or alkali. The acid may be organic or inorganic acids such as, for example, hydrochloric acid, sulfuric acid, phosphoric acid, acetic acid, methanesulfonic acid, oxalic acid and lactic acid. The carboxylic acid metal salts may be, for example, sodium, potassium, magnesium, calcium, aluminum, cerium, chromium, cobalt, copper, iron, zinc, platinum and silver salts.

The compound of the formula (I), hydrates and salts thereof may be used as medicines in the conventional form of pharmaceutical preparations, which may be, for example, tablets, capsules, powder, ointments, suppositories, injections or eye drops, suitable for peroral, parenteral, enteral or local administration.

The following examples will further illustrate the present invention without, however, limiting it thereto.

REFERENCE EXAMPLE 1

3-Aminomethyl-4-methylpyrrolidine

A solution of ethyl 3-methyl-2-oxo-4-pyrrolidinecarboxylate [Chem. Pharm. Bull., 24, 1362 (1976)] (5 g) in methanol (100 ml) saturated with ammonia gas left at room temperature for 4 days. After the reaction mixture was concentrated and the residue was recrystallized from ethanol to give 3-methyl-2-oxo-4-pyrrolidinecarboxamide (3.4 g), mp 169°–171° C.

Analysis (%) for $C_6H_{10}N_2O_2$, Calcd. (Found): C, 50.70 (50.83), H, 7.09 (7.23); N, 19.70 (19.53).

To a suspension of lithium aluminum hydride (2.5 g) in tetrahydrofuran (50 ml) was gradually added 3-methyl-2-oxo-4-pyrrolidinecarboxamide (3.23 g) under stirring. After stirring for 2 hours, the suspension was cooling under ice-water bath and to this was added water (3.6 ml). The resulting precipitate was filtered off and extracted the insoluble material with hot ethanol (90 ml). The filtrate and extract solution were combined and concentrated. The residue was distilled under reduced pressure to give the title compound (1.75 g), bp 71°–86° C./29 mmHg.

REFERENCE EXAMPLE 2

1-Benzyl-cis-3-t-butoxycarbonylamino-4-methylpyrrolidine

To a suspension of sodium hydride (2.30 g) in absolute dioxane (100 ml) was added dropwise ethyl 3-methyl-2-oxo-4-pyrrolidinecarboxylate (13.68 g) with stirring at room temperature. After stirring for 30 minutes, to a reaction mixture was added benzylbromide (16.42 g) during 20 minutes, then stirred for 2 hours and allowed to stand overnight at room temperature. The reaction mixture was poured into ice-water (100 ml) and extracted with chloroform, washed with water, dried over anhydrous sodium sulfate and concentrated. The residue was purified by vacuum distillation to give ethyl 1-benzyl-3-methyl-2-oxo-4-pyrrolidinecarboxylate (16.86 g), bp 155°–185° C./2 mmHg.

A mixture of ethyl 1-benzyl-3-methyl-2-oxo-4-pyrrolidinecarboxylate (16.0 g), 80% hydrazinehydrate (16 ml) and ethanol (16 ml) was refluxed for 5 hours with stirring and then concentrated. The removal of excess hydrazine from the residue by azeotrope with ethanol and benzene gave 1-benzyl-3-methyl-2-oxo-4-pyrrolidinecarboxylic acid hydrazide (16.38 g) as colorless viscous oil.

To a mixture of this oil in ice-water (100 ml) contain concentrated hydrochloric acid (6.5 ml) and ether (100 ml) was added dropwise a solution of sodium nitrite (4.92 g) in water (10 ml) with stirring for 5 minutes at 0°–3° C. After stirring for 20 minutes, the organic layer was separated, washed with ice-water and chilled saturated aqueous sodium bicarbonate solution successively, dried over anhydrous sodium sulfate and concentrated below room temperature. To the resulting residue was added t-butanol (100 ml) and refluxed for 6 hours. The reaction mixture was concentrated to give 1-benzyl-4-t-butoxycarbonylamino-3-methyl-2-oxopyrrolidine (14.96 g).

To a suspension of lithium aluminum hydride (3.61 g) in absolute ether (150 ml) was added dropwise a solution of 1-benzyl-4-t-butoxycarbonylamino-3-methyl-2-oxopyrrolidine (14.46 g) in absolute ether (100 ml) with stirring for an hour at $-5°\sim 3°$ C. After stirring for an hour at 0° C., the reaction mixture as poured into ice-water and added 50% aqueous sodium hydroxide solution, the organic layer was separated, washed with water and saturated aqueous sodium chloride successively, dried over anhydrous sodium sulfate and concentrated. The residue was recrystallized from acetonitrile to give the title compound (4.87 g) as colorless prisms, mp 134°–140° C.

Analysis (%) for $C_{17}H_{26}N_2O_2$, Calcd. (Found): C, 70.31 (70.61); H, 9.03 (9.08); N, 9.64 (9.89).

NMR ($\delta$ in CDCl$_3$): 1.08 (3H, d, J=6 HZ, —CH$_3$), 1.43 (9H, s, —C(CH$_3$)$_3$), 1.87 (1H, m,

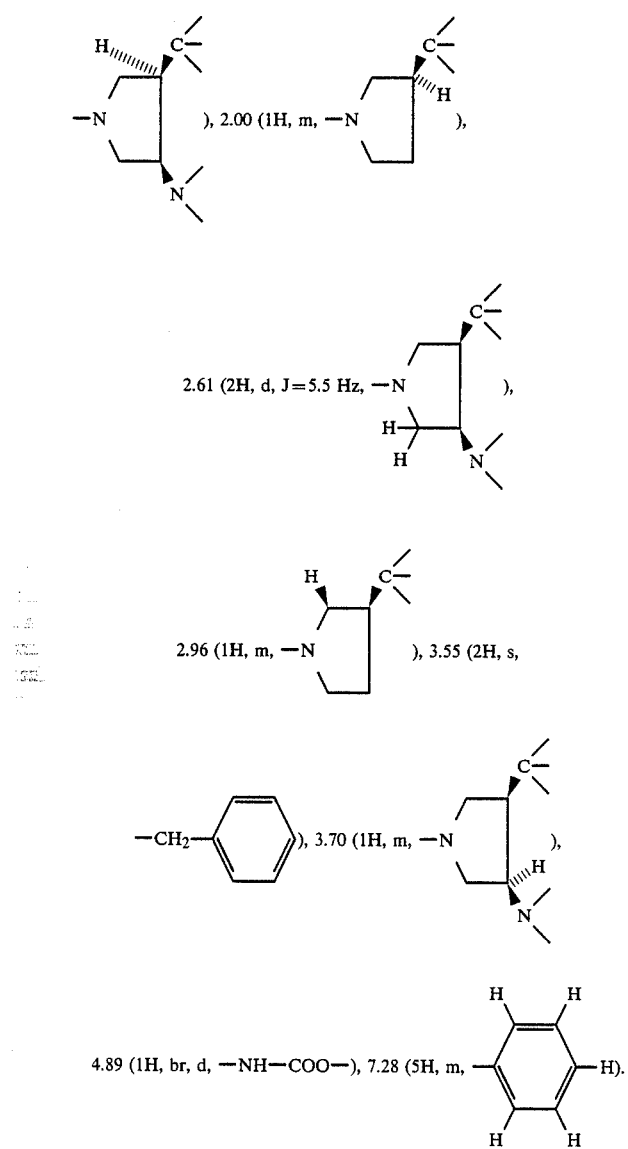

REFERENCE EXAMPLE 3 cis-3-t-Butoxycarbonylamino-4-methylpyrrolidine

A suspension of 1-benzyl-cis-3-t-butoxycarbonylamino-4-methylpyrrolidine (5.37 g) and 10% palladium-on-charcoal (2.70 g) in ethanol (50 ml) was shaken with hydrogen were absorbed under elevated pressure (100 kg/cm$^2$) at room temperature for 22 hours. The catalyst was removed by filtration and the filtrate was evaporated to give the title compound (3.25 g). The compound was gradually solidified at room temperature.

NMR ($\delta$ in CDCl$_3$): 1.07 (3H, d, J=7.0 Hz, —CH$_3$), 1.45 (9H, s, —C(CH$_3$)$_3$), 1.68–2.15 (1H, m,

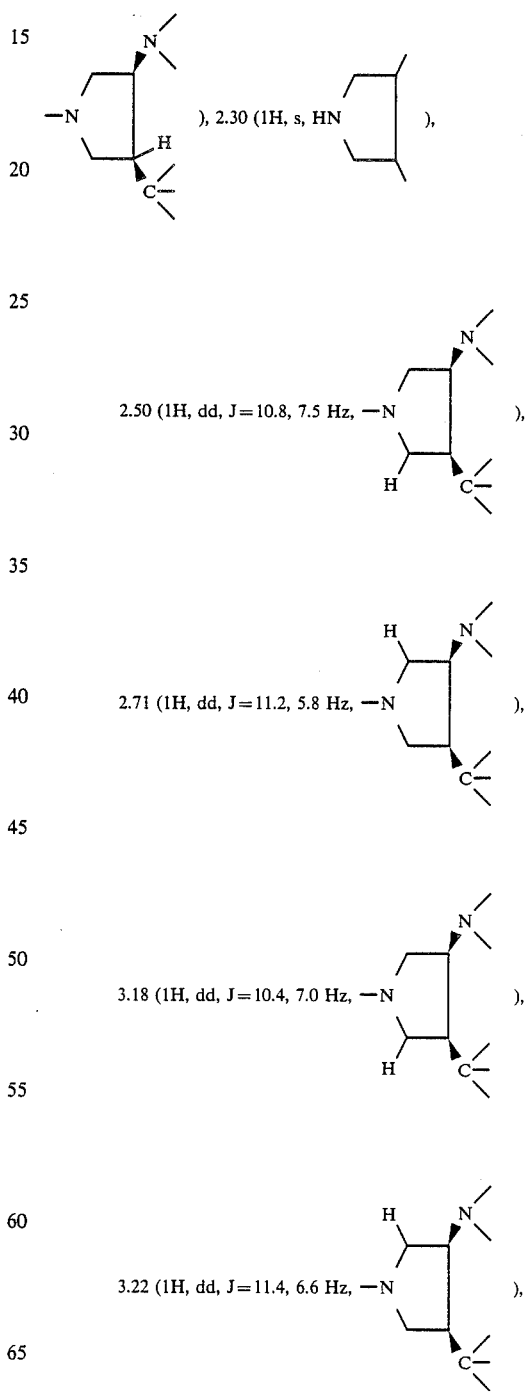

3.42–3.78 (1H, m, —N 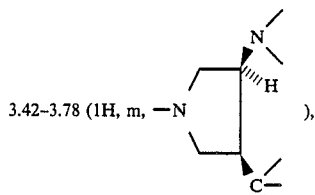), 4.60–4.92 (1H, br, —N 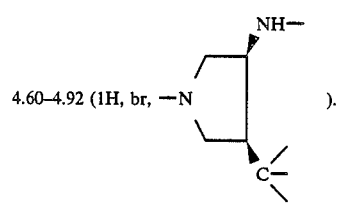).

REFERENCE EXAMPLE 4

1-Benzyl-trans-3-t-butoxycarbonylamino-4-methylpyrrolidine

To a solution of benzylamine (75 g) in ethanol (150 ml) was added ethyl methacrylate (240 g) and refluxed for 23 hours. The reaction mixture was evaporated and the resulting residue was distilled under reduced pressure to give N-(2-ethoxycarbonylpropyl)benzylamine (93.3 g) as colorless liquid, bp 122° C./4 mmHg.

To a solution of this liquid in ethanol (140 ml) was added ethyl bromoacetate (96.5 g) and refluxed for 2 hours. After cooling, the reaction mixture was poured into ice-water (500 ml) and alkalized with 40% aqueous sodium hydroxide solution, and extracted with benzene. The organic layer was washed with diluted aqueous sodium hydroxide solution and water successively, dried over anhydrous sodium sulfate and concentrated. The residue was distilled under reduced pressure to give N-ethoxycarbonylmethyl-N-(2-ethoxycarbonylpropyl)benzylamine (114.4 g) as yellow liquid, bp 147° C./3 mmHg.

A solution of this oil (111.2 g) in absolute benzene (100 ml) was added dropwise to a suspension of sodium ethoxide (27.5 g) in absolute benzene (150 ml) for 30 minutes at 10° C. After stirring for 1.5 hours at same temperature, the reaction mixture was extracted with concentrated hydrochloric acid (100 ml). The hydrochloric acid layer was refluxed for 28 hours and the insoluble material was removed by filtration and the filtrate was concentrated. To the resulting residue was added water (300 ml) and alkalized with 40% aqueous sodium hydroxide (pH 10), and extracted with ether. The organic layer was washed with saturated aqueous sodium chloride solution, dried over anhydrous sodium sulfate and concentrated. The residue was distilled under reduced pressure to give 1-benzyl-4-methyl-3-pyrrolidone (41.8 g) as yellow liquid, bp 104°–107° C.

To a solution of hydroxylamine hydrochloride (78.3 g) in water (300 ml) was added dropwise a solution of this liquid (41.8 g) in ethanol (300 ml) at 20°–25° C. for 30 minutes. sodium bicarbonate (63.2 g) was added to the mixture, and the mixture was stirred for 30 minutes at room temperature. The reaction mixture was allowed to stand overnight at 5° C., then 150 ml of water was added to the mixture and extracted with dichloromethane. The organic layer was washed with water, dried over anhydrous sodium sulfate and concentrated to give 1-benzyl-3-hydroxyimino-4-methylpyrrolidine (45.7 g) as colorless solid, mp 85°–94° C.

A suspension of this solid (40 g) and Raney nickel (W7, −12.5 g) in methanol containing ammonia was shaken with hydrogen were absorbed under elevated pressure (80 kg/cm²) at room temperature for 12 hours. The catalyst was removed by filtration and the filtrate was evaporated. The resulting residue was distilled under reduced pressure to give 3-amino-1-benzyl-4-methylpyrrolidine (31.0 g) as colorless liquid, bp 100°–104° C./2 mmHg.

This liquid (10 g) was added to wide mouth container and stirred with air at room temperature. To the resulting precipitate was added ether (50 ml) and collected by filtration to give trans-3-amino-1-benzyl-4-methylpyrrolidine hydrocarbonate (4.1 g), mp 74°–80° C.

To a solution of trans-3-amino-1-benzyl-4-methylpyrrolidine hydrocarbonate (4.0 g) and triethylamine (3.2 g) in 50% aqueous dioxane (50 ml) was added t-butoxycarbonyloxyimino-2-phenylacetonitrile (Boc-ON, 5.8 g) with stirring at room temperature. After stirring for 3 hours, the reaction mixture was poured into ice-water and extracted with ether. The organic layer was washed 1N aqueous sodium hydroxide solution and saturated aqueous sodium chloride solution successively, dried over anhydrous sodium sulfate and concentrated. The residue was purified by silica-gel column chromatography eluting with benzene to chloroform:methanol:concentrated aqueous ammonia (10:10:1) to give the title compound (5.24 g). Recrystallization from hexane gave colorless needles (5.04 g), mp 79°–80° C.

Analysis (%) for $C_{17}H_{26}N_2O_2$, Calcd. (Found): C, 70.31 (70.26); H, 9.02 (8.90); N, 9.65 (9.69).

NMR (δ in CDCl₃): 0.93 (3H, d, J=6.6 Hz, —CH₃), 1.44 (9H, s, —C(CH₃)₃), 2.06–2.49 (3H, m,

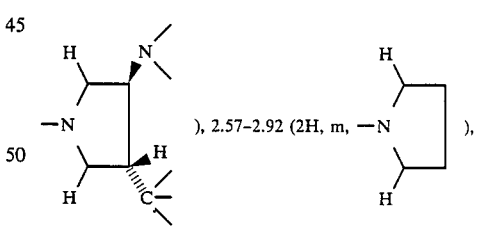), 2.57–2.92 (2H, m, —N 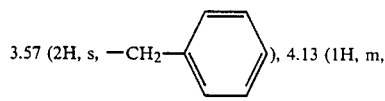), 3.57 (2H, s, —CH₂—⌬), 4.13 (1H, m,

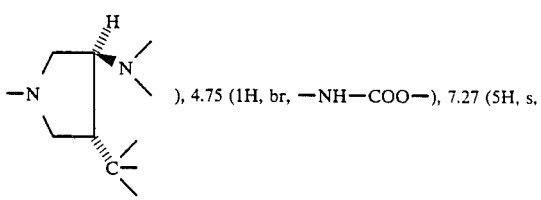), 4.75 (1H, br, —NH—COO—), 7.27 (5H, s,

-continued

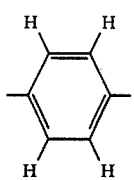

REFERENCE EXAMPLE 5 trans-3-t-Butoxycarbonylamino-4-methylpyrrolidine

A suspension of 1-benzyl-trans-3-t-butoxycarbonylamino-4-methylpyrrolidine (4.8 g) and 10% palladium-on-charcoal (1.8 g) in ethanol (40 ml) was shaken with hydrogen were absorbed under elevated pressure (100 kg/cm$^2$) at 50°-70° C. for 6.5 hours. The catalyst was removed by filtration and the filtrate was evaporated to give the title compound (3.09 g) as brown oil. This oil was gradually solidified at room temperature.

NMR (δ in CDCl$_3$): 0.97 (3H, d, J=6.6 Hz, —CH$_3$), 1.45 (9H, s, —C(CH$_3$)$_3$), 2.16 (1H, br, s,

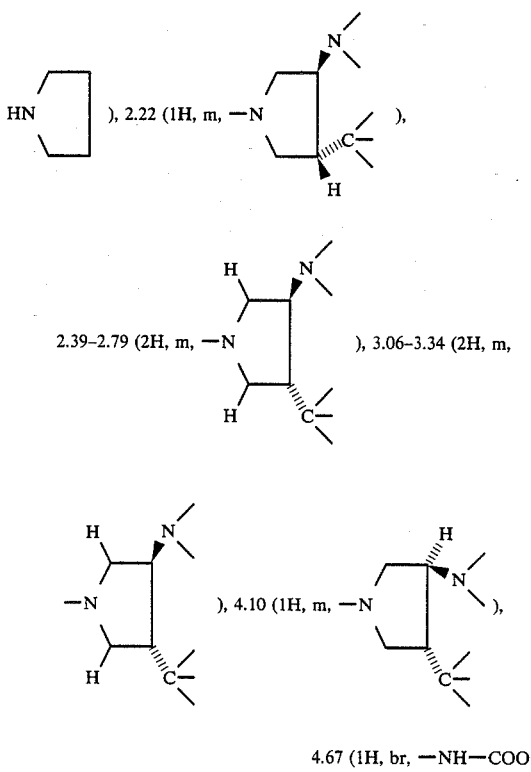

4.67 (1H, br, —NH—COO—).

EXAMPLE 1

7-(3-Aminomethyl-4-methyl-1-pyrrolidinyl)-8-chloro-1-cyclopropyl-6-fluoro-1,4-dihydro-4-oxo-3-quinolinecarboxylic acid A mixture of 8-chloro-1-cyclopropyl-6,7-difluoro-1,4-dihydro-4-oxo-3-quinolinecarboxylic acid (0.6 g), anhydrous acetonitrile (5 ml), 3-aminomethyl-4-methylpyrrolidine (0.27 g) and 1,8-diazabicyclo[5,4,0]-7-undecene (DBU; 0.3 g) was refluxed for an hour and then stirred at room temperature for 7 hours. The resulting precipitate was collected by filtration and recrystallized from chloroform-methanol-concentrated aqueous ammonia (10:10:1) to give the title compound (0.26 g) as colorless prisms, mp 235°-238° C.

Analysis (%) for C$_{19}$H$_{21}$ClFN$_3$O$_3$.H$_2$O, Calcd. (Found): C, 55.41 (55.46); H, 5.63 (5.73); N, 10.20 (10.19).

EXAMPLE 2

7-(3-Aminomethyl-4-methyl-1-pyrrolidinyl)-1-cyclopropyl-6,8-difluoro-1,4-dihydro-4-oxo-3-quinolinecarboxylic acid A mixture of 1-cyclopropyl-6,7,8-trifluoro-1,4-dihydro-4-oxo-3-quinolinecarboxylic acid (0.6 g), anhydrous acetonitrile (5 ml), 3-aminomethyl-4-methylpyrrolidine (0.29 g) and DBU (0.33 g) was refluxed for an hour and then stirred at room temperature for 2 hours and allowed to stand overnight. The resulting precipitate was collected by filtration and recrystallized from chloroform-methanol-concentrated aqueous ammonia (10:10:1) to give the title compound (0.45 g) as colorless prisms, mp 249°-252.5° C.

Analysis (%) for C$_{19}$H$_{21}$F$_2$N$_3$.H$_2$O, Calcd. (Found): C, 57.72 (57.41); H, 5.86 (5.70); N, 10.63 (10.57).

EXAMPLE 3

7-(3-Aminomethyl-4-methyl-1-pyrrolidinyl)-1-ethyl-6,8-difluoro-1,4-dihydro-4-oxo-3-quinolinecarboxylic acid A mixture of 1-ethyl-6,7,8-trifluoro-1,4-dihydro-4-oxo-3-quinolinecarboxylic acid (0.5 g), anhydrous acetonitrile (5 ml), 3-aminomethyl-4-methylpyrrolidine (0.22 g) and DBU (0.28 g) was refluxed for an hour and then stirred at room temperature for 3 hours. The resulting precipitate was collected by filtration and washed with ether to give the title compound (0.39 g) as pale yellow powder, mp 222°-224° C.

Analysis (%) for C$_{18}$H$_{21}$F$_2$N$_3$O$_3$.H$_2$O, Calcd. (Found): C, 56.39 (56.46); H, 6.05 (5.85); N, 10.96 (11.02).

EXAMPLE 4

7-(3-Aminomethyl-4-methyl-1-pyrrolidinyl)-6,8-difluoro-1-(2-fluoroethyl)-1,4-dihydro-4-oxo-3-quinolinecarboxylic acid A mixture of 6,7,8-trifluoro-1-(2-fluoroethyl)-1,4-dihydro-4-oxo-3-quinolinecarboxylic acid (0.5 g), anhydrous acetonitrile (5 ml), 3-aminomethyl-4-methylpyrrolidine (0.21 g) and DBU (0.26 g) was refluxed for an hour and then stirred at room temperature for 5 hours. The resulting precipitate was collected by filtration and washed with ether to give the title compound (0.45 g) as pale yellow powder, mp 228°-232° C.

Analysis (%) for C$_{18}$H$_{20}$F$_3$N$_3$O$_3$.¼H$_2$O, Calcd. (Found): C, 55.73 (55.74); H, 5.32 (5.28); N, 10.83 (11.00).

EXAMPLE 5

7-(3-Aminomethyl-4-methyl-1-pyrrolidinyl)-1-ethyl-6-fluoro-1,4-dihydro-4-oxo-3-quinolinecarboxylic acid A mixture of 7-chloro-1-ethyl-6-fluoro-1,4-dihydro-4-oxo-3-quinolinecarboxylic acid (0.5 g), β-picoline (11 ml) and 3-aminomethyl-4-methylpyrrolidine (0.5 g) was refluxed for 8.5 hours, then the reacting mixture was cooled to room temperature. To the mixture was added concentrated aqueous ammonia (100 ml) and concentrated under reduced pressure. To the residue was added dichloromethane-ether (1:3, 37 ml), the resulting precipitate was collected by filtration, washed with ethanol-ether (1:3), recrystallized from ethanol and further recrystallized from chloroform-methanol-concentrated aqueous ammonia (10:10:1) to give the title compound (0.14 g) as pale yellow powder, mp 245°–248° C.

Analysis (%) for $C_{18}H_{22}FN_3O_3.5/4\ H_2O$, Calcd. (Found): C, 58.45 (58.67); H, 6.68 (6.38); N, 11.36 (11.03).

EXAMPLE 6

7-(3-t-Butoxycarbonylamino-4-methyl-1-pyrrolidinyl)-8-chloro-1-cyclopropyl-6-fluoro-1,4-dihydro-4-oxo-3-quinolinecarboxylic acid A mixture of 8-chloro-1-cyclopropyl-6,7-difluoro-1,4-dihydro-4-oxo-3-quinolinecarboxylic acid (0.5 g), anhydrous acetonitrile (5 ml), 3-t-butoxycarbonylamino-4-methylpyrrolidine (0.5 g) and DBU (0.25 g) was refluxed for an hour. The reacting mixture was concentrated under reduced pressure, to the resulting residue was added acetonitrile-ether (1:1) to crystallize and the precipitate was collected by filtration. This precipitate was recrystallized from dichloromethane-methanol to give the title compound (0.4 g) as pale yellow powder, mp 213°–215° C.

Analysis (%) for $C_{23}H_{27}ClFN_3O_5$, Calcd. (Found): C, 57.56 (57.66); H, 5.67 (5.70); N, 8.76 (8.81).

EXAMPLE 7

7-(3-Amino-4-methyl-1-pyrrolidinyl)-8-chloro-1-cyclopropyl-6-fluoro-1,4-dihydro-4-oxo-3-quinolinecarboxylic acid 7-(3-t-Butoxycarbonylamino-4-methyl-1-pyrrolidinyl)-8-chloro-1-cyclopropyl-6-fluoro-1,4-dihydro-4-oxo-3-quinolinecarboxylic acid (0.35 g) was dissolved in the mixture of methanol (5 ml) and concentrated hydrochloric acid (5 ml) and stirred at room temperature for 30 minutes. After the reacting mixture was concentrated under reduced pressure, the resulting residue was dissolved in ethanol (10 ml) and neutralized with concentrated aqueous ammonia. The resulting precipitate was collected by filtration, washed with water and recrystallized from chloroformmethanol-concentrated aqueous ammonia to give the title compound (0.07 g) as pale yellow powder, mp 231°–234° C.

Analysis (%) for $C_{18}H_{19}ClFN_3O_3$, Calcd. (Found): C, 56.92 (56.87); H, 5.04 (5.17); N, 11.06 (11.03).

EXAMPLE 8

7-[3-(N-Acetyl-N-methylamino)-4-methyl-1-pyrrolidinyl]-1-cyclopropyl-6,8-difluoro-1,4-dihydro-4-oxo-3-quinolinecarboxylic acid A mixture of 1-cyclopropyl-6,7,8-trifluoro-1,4-dihydro-4-oxo-3-quinolinecarboxylic acid (0.5 g), anhydrous acetonitrile (5 ml), 3-(N-acetyl-N-methylamino)-4-methylpyrrolidine (0.42 g) and DBU (0.27 g) was refluxed for an hour and allowed to stand overnight. The resulting precipitate was collected by filtration and washed with acetonitrile-ether to give the title compound (0.56 g) as pale yellow powder.

IR$\nu_{MAX}^{KBr}$cm$^{-1}$: 1730

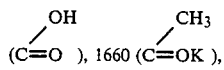

1630 (C=O).

EXAMPLE 9

1-Cyclopropyl-6,8-difluoro-1,4-dihydro-7-(3-methylamino-4-methyl-1-pyrrolidinyl)-4-oxo-3-quinolinecarboxylic acid hydrochloride 7-[3-(N-Acetyl-N-methylamino)-4-methyl-1-pyrrolidinyl]-1-cyclopropyl-6,8-difluoro-1,4-dihydro-4-oxo-3-quinolinecarboxylic acid (0.56 g) was dissolved in 20% aqueous hydrochloric acid solution (5 ml) and refluxed for 2 hours. Then the reacting mixture was concentrated under reduced pressure, to the resulting residue was added ethanol (10 ml) and crystallized with cooling. The resulting precipitate was collected by filtration and recrystallized from methanol to give the title compound as pale yellow powder, mp 242°–246° C.

Analysis (%) for $C_{19}H_{21}F_2N_3O_3.HCl.2H_2O$: Calcd. (Found): C, 50.73 (50.57); H, 5.83 (5.73); N, 9.34 (9.40).

EXAMPLE 10

7-(3-t-Butoxycarbonylamino-4-methyl-1-pyrrolidinyl)-1-cyclopropyl-6,8-difluoro-1,4-dihydro-4-oxo-3-quinolinecarboxylic acid A mixture of 1-cyclopropyl-6,7,8-trifluoro-1,4-dihydro-4-oxo-3-quinolinecarboxylic acid (0.5 g), anhydrous acetonitrile (5 ml), 3-t-butoxycarbonylamino-4-methylpyrrolidine (0.53 g) and DBU (0.27 g) was refluxed for an hour. After cooling in a refrigerator, the resulting precipitate was collected by filtration and washed with acetonitrile and ether successively to give the title compound (0.32 g) as pale yellow powder, mp 230°–231° C.

IR$\nu_{MAX}^{KBr}$cm$^{-1}$: 3350 (NH), 1700

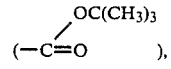

1630 (C=O)

EXAMPLE 11

7-(3-Amino-4-methyl-1-pyrrolidinyl)-1-cyclopropyl-6,8-difluoro-1,4-dihydro-4-oxo-3-quinolinecarboxylic acid hydrochloride 7-(3-t-Butoxycarbonylamino-4-methyl-1-pyrrolidinyl)-1-cyclopropyl-6,8-difluoro-1,4-dihydro-4-oxo-3-quinolinecarboxylic acid (0.27 g) was dissolved in a mixture of methanol (5 ml) and concentrated hydrochloric acid (5 ml) and stirred at room temperature for 30 minutes. After the reacting mixture was concentrated under reduced pressure, the resulting residue was dissolved in ethanol (10 ml) and crystallized with cooling. The resulting precipitate was recrystallized from methanol to give the title compound (0.14 g) as pale yellow powder, mp 272°–274° C.

Analysis (%) for $C_{18}H_{19}F_2N_3O_3.HCl.\frac{1}{2}H_2O$: Calcd. (Found): C, 52.88 (52.66); H, 5.18 (5.16); N, 10.28 (10.20).

EXAMPLE 12

8-Chloro-1-cyclopropyl-6-fluoro-1,4-dihydro-7-(3-methylaminomethyl-4-methyl-1-pyrrolidinyl)-4-oxo-3-quinolinecarboxylic acid A mixture of 8-chloro-1-cyclopropyl-6,7-difluoro-1,4-dihydro-4-oxo-3-quinolinecarboxylic acid (0.5 g), anhydrous acetonitrile (5 ml), 3-methylaminomethyl-4-methylpyrrolidine (0.32 g) and DBU (0.25 g) was refluxed for an hour and allowed to stand overnight at room temperature. The resulting precipitate was collected by filtration, washed with acetonitrile and ether successively and recrystallized from chloroform-methanol-concentrated aqueous ammonia to give the title compound (0.31 g) as pale yellow powder, mp 253°–255° C.

Analysis (%) for $C_{20}H_{23}ClFN_3O_3 \cdot \frac{1}{2}H_2O$, Calcd. (Found): C, 58.25 (58.36); H, 5.74 (5.96); N, 10.19 (10.10).

EXAMPLE 13

1-Cyclopropyl-6,8-difluoro-1,4-dihydro-7-(3-methylaminomethyl-4-methyl-1-pyrrolidinyl)-4-oxo-3-quinolinecarboxylic acid A mixture of 1-cyclopropyl-6,7,8-trifluoro-1,4-dihydro-4-oxo-3-quinolinecarboxylic acid (0.5 g), anhydrous acetonitrile (5 ml), 3-methylaminomethyl-4-methylpyrrolidine (0.34 g) and DBU (0.27 g) was refluxed for an hour and allowed to stand overnight at room temperature. The resulting precipitate was collected by filtration, washed with acetonitrile and ether successively and recrystallized from chloroform-methanol-concentrated aqueous ammonia to give the title compound (0.41 g) as white powder, mp 252°–254° C.

Analysis (%) for $C_{20}H_{23}F_2N_3O_3 \cdot \frac{3}{4}H_2O$, Calcd. (Found): C, 59.38 (59.14); H, 6.10 (6.09); N, 10.39 (10.34).

EXAMPLE 14

8-Chloro-1-cyclopropyl-7-(3-ethylaminomethyl-4-methyl-1-pyrrolidinyl)-6-fluoro-1,4-dihydro-4-oxo-3-quinolinecarboxylic acid A mixture of 8-chloro-1-cyclopropyl-6,7-difluoro-1,4-dihydro-4-oxo-3-quinolinecarboxylic acid (0.5 g), anhydrous acetonitrile (5 ml), 3-ethylaminomethyl-4-methylpyrrolidine (0.36 g) and DBU (0.25 g) was refluxed for 2 hours and allowed to stand overnight at room temperature. The resulting precipitate was collected by filtration, washed with acetonitrile and ether successively and recrystallized from chloroform-methanol-concentrated aqueous ammonia to give the title compound (0.56 g) as pale yellow powder, mp 254°–257° C.

Analysis (%) for $C_{21}H_{25}ClFN_3O_3 \cdot \frac{3}{4}H_2O$, Calcd. (Found): C, 57.92 (57.75); H, 6.13 (6.03); N, 9.65 (9.66).

EXAMPLE 15

1-Cyclopropyl-7-(3-ethylaminomethyl-4-methyl-1-pyrrolidinyl)-6,8-difluoro-1,4-dihydro-4-oxo-3-quinolinecarboxylic acid A mixture of 1-cyclopropyl-6,7,8-trifluoro-1,4-dihydro-4-oxo-3-quinolinecarboxylic acid (0.5 g), anhydrous acetonitrile (5 ml), 3-ethylaminomethyl-4-methylpyrrolidine (0.38 g) and DBU (0.27 g) was refluxed for an hour and allowed to stand overnight at room temperature. The resulting precipitate was collected by filtration, washed with acetonitrile and ether successively and recrystallized from chloroform-methanol-concentrated aqueous ammonia to give the title compound (0.47 g) as pale yellow powder, mp 224°–226° C.

Analysis (%) for $C_{21}H_{25}F_2N_3O_3 \cdot \frac{1}{4}H_2O$, Calcd. (Found): C, 61.53 (61.81); H, 6.27 (6.31); N, 10.25 (10.31).

EXAMPLE 16

7-(cis-3-Amino-4-methyl-1-pyrrolidinyl)-8-chloro-1-cyclopropyl-6-fluoro-1,4-dihydro-4-oxo-3-quinolinecarboxylic acid A mixture of 8-chloro-1-cyclopropyl-6,7-difluoro-1,4-dihydro-4-oxo-3-quinolinecarboxylic acid (1.8 g), anhydrous acetonitrile (18 ml), cis-3-t-butoxycarbonylamino-4-methylpyrrolidine (reference example 3; 1.81 g) and DBU (0.90 g) was refluxed for an hour. The resulting mixture was concentrated under reduced pressure, the resulting residue was dissolved in chloroform and washed with 10% aqueous citric acid solution. The chloroform layer was further washed with saturated aqueous sodium chloride solution, dried over anhydrous sodium sulfate and concentrated under reduced pressure. The resulting residue was dissolved in hot methanol (25 ml) and, after cooling, the resulting precipitate was collected by filtration. Then this precipitate was suspended in methanol (18 ml), to this solution was added concentrated hydrochloric acid (18 ml) dropwise and stirred at room temperature for 15 minutes. The reacting mixture was neutralized with concentrated aqueous ammonia, after cooling, the resulting precipitate was collected by filtration and washed with water, methanol and ether successively to give the title compound (1.67 g) as white powder, mp 240°–243° C. (decompd.).

Analysis (%) for $C_{18}H_{19}ClFN_3O_3$, Calcd. (Found): C, 56.92 (57.13); H, 5.04 (5.06); N, 11.06 (10.73).

EXAMPLE 17

7-(trans-3-Amino-4-methyl-1-pyrrolidinyl)-8-chloro-1-cyclopropyl-6-fluoro-1,4-dihydro-4-oxo-3-quinolinecarboxylic acid A mixture of 8-chloro-1-cyclopropyl-6,7-difluoro-1,4-dihydro-4-oxo-3-quinolinecarboxylic acid (2.2 g), anhydrous acetonitrile (22 ml), trans-3-t-butoxycarbonylamino-4-methylpyrrolidine (reference example 5; 2.4 g) and DBU (1.22 g) was refluxed for 5 hours. The reacting mixture was concentrated under reduced pressure, the resulting residue was dissolved in chloroform and washed with 10% aqueous citric acid solution. The chloroform layer was further washed with saturated aqueous sodium chloride solution, dried over anhydrous sodium sulfate and concentrated under reduced pressure. The resulting residue was dissolved in hot methanol (20 ml) and, after cooling, the resulting precipitate was collected by filtration to give 7-(trans-3-t-butoxycarbonylamino-4-methyl-1-pyrrolidinyl)-8-chloro-1-cyclopropyl-6-fluoro-1,4-dihydro-4-oxo-3-quinolinecarboxylic acid (3.62 g) as yellow needle, mp 210°–213° C. (decompd.).

Analysis (%) for $C_{23}H_{27}ClFN_3O_5$, Calcd. (Found): C, 57.56 (57.33); H, 5.67 (5.61); N, 8.76 (8.76).

Then this precipitate (3.55 g) was suspended in methanol (25 ml), to this solution was added concentrated hydrochloric acid (25 ml) dropwise and stirred at room temperature for an hour. The reacting mixture was neutralized with concentrated aqueous ammonia after cooling, the resulting precipitate was collected by filtration and washed with water, methanol and ether successively to give the title compound (2.19 g) as white yellowish powder, mp 183°–187° C.

Analysis (%) for $C_{18}H_{19}ClFN_3O_3 \cdot \frac{1}{4}H_2O$, Calcd. (Found): C, 56.25 (56.47); H, 5.11 (4.95); N, 10.93 (10.97).

EXAMPLE 18

7-(trans-3-Amino-4-methyl-1-pyrrolidinyl)-1-cyclopropyl-6,8-difluoro-1,4-dihydro-4-oxo-3-quinolinecarboxylic acid A mixture of 1-cyclopropyl-6,7,8-trifluoro-1,4-dihydro-4-oxo-3-quinolinecarboxylic acid (0.4 g), anhydrous acetonitrile (4 ml), trans-3-t-butoxycarbonylamino-4-methylpyrrolidine (0.43 g) and DBU (0.22 g) was refluxed for an hour. After cooling, the resulting precipitate was collected by filtration and washed with acetonitrile and ethanol successively to give 7-(trans-3-t-butoxycarbonylamino-4-methyl-1-pyrrolidinyl)-1-cyclopropyl-6,8-difluoro-1,4-dihydro-4-oxo-3-quinolinecarboxylic acid (0.34 g) as white yellowish powder, mp 237°–240° C. (decompd.).

Analysis (%) for $C_{23}H_{27}F_2N_3O_5$, Calcd. (Found): C, 59.60 (59.31); H, 5.87 (5.81); N, 9.07 (9.01).

Then this precipitate (0.41 g) was suspended in trifluoroacetic acid (5 ml) and stirred at room temperature for 2 hours. The reacting mixture was concentrated under reduced pressure, to this residue was added ice-water (10 ml) and dissolved in 1N aqueous sodium hydroxide solution. After filtration insoluble materials off, the resulting solution was neutralized with acetic acid. The resulting precipitate was collected by filtration and recrystallized form methanol-chloroform to give the title compound (0.15 g) as white yellowish powder, mp 257°–260° C.

Analysis (%) for $C_{18}H_{19}F_2N_3O_3 \cdot \frac{3}{4}H_2O$, Calcd. (Found): C, 57.37 (57.26); H, 5.48 (5.47); N, 11.15 (11.06).

EXAMPLE 19

7-(cis-3-t-Butoxycarbonylamino-4-methyl-1-pyrrolidinyl)-1-cyclopropyl-6,8-difluoro-1,4-dihydro-4-oxo-3-quinolinecarboxylic acid A mixture of 1-cyclopropyl-6,7,8-trifluoro-1,4-dihydro-4-oxo-3-quinolinecarboxylic acid (0.5 g), anhydrous acetonitrile (6 ml), cis-3-t-butoxycarbonylamino-4-methylpyrrolidine (0.53 g) and DBU (0.27 g) was refluxed for an hour and the resulting precipitate was collected by filtration to give the title compound (0.72 g) as pale yellowish powder, mp 229°–230° C. Analysis (%) for $C_{23}H_{27}F_2N_3O_5$, Calcd. (Found): C, 59.60 (59.47); H, 5.87 (5.85); N, 9.07 (9.01).

EXAMPLE 20

7-(cis-3-Amino-4-methyl-1-pyrrolidinyl)-1-cyclopropyl-6,8-difluoro-1,4-dihydro-4-oxo-3-quinolinecarboxylic acid hydrochloride A mixture of 7-(cis-3-t-butoxycarbonylamino-4-methyl-1-pyrrolidinyl)-1-cyclopropyl-6,8-difluoro-1,4-dihydro-4-oxo-3-quinolinecarboxylic acid (0.3 g) in ethanol (5 ml) and ethanolic hydrochloride (6 ml) was stirred for 2 hours at room temperature and then concentrated. To the residue was added ethanol and the resulting precipitate was collected by filtration and washed with ethanol to give the title compound (0.21 g) as pale yellowish powder, mp 274°–275° C. (decompd.).

Analysis (%) for $C_{18}H_{19}F_2N_3O_3 \cdot HCl \cdot \frac{3}{8}H_2O$, Calcd. (Found): C, 52.49 (52.54); H, 5.22 (5.13); N, 10.20 (10.09).

EXAMPLE 21

7-(cis-3-Amino-4-methyl-1-pyrrolidinyl)-8-bromo-1-cyclopropyl-6-fluoro-1,4-dihydro-4-oxo-3-quinolinecarboxylic acid A mixture of 8-bromo-1-cyclopropyl-6,7-difluoro-1,4-dihydro-4-oxo-3-quinolinecarboxylic acid (0.19 g), cis-3-t-butoxycarbonylamino-4-methylpyrrolidine (0.14 g), DBU (0.095 g) and anhydrous acetonitrile (5 ml) was refluxed for 2 hours and then concentrated. The resulting residue was dissolved in chloroform (70 ml), washed with 10% aqueous citric acid solution, water successively, dried over anhydrous sodium sulfate and then concentrated. To the resulting oily residue was added hot methanol to crystallize and cooled. The resulting precipitate was collected by filtration, added to the mixture of concentrated hydrochloric acid-methanol (1:1, 3 ml) and stirred for 2.5 hours under elevated temperature. The reaction mixture was neutralized with concentrated aqueous ammonia, the resulting precipitate was collected by filtration, washed with ice-water and recrystallized from dichloromethane-methanol-concentrated aqueous ammonia (10:10:1) to give the title compound (0.06 g) as yellow prisms, mp 225°–226.5° C. (decompd.).

Analysis (%) for $C_{18}H_{19}BrFN_3O_3$, Calcd. (Found): C, 50.96 (51.05); H, 4.51 (4.71); N, 9.90 (9.98).

EXAMPLE 22

7-(cis-3-Amino-4-methyl-1-pyrrolidinyl)-1-ethyl-6,8-difluoro-1,4-dihydro-4-oxo-3-quinolinecarboxylic acid A mixture of 1-ethyl-6,7,8-trifluoro-1,4-dihydro-4-oxo-3-quinolinecarboxylic acid (1.0 g), cis-3-t-butoxycarbonylamino-4-methylpyrrolidine (0.89 g), DBU (0.62 g) and anhydrous acetonitrile (30 ml) was refluxed for 2 hours and then concentrated. The resulting residue was dissolved in chloroform (50 ml), washed with 10% aqueous citric acid solution and water successively, dried over anhydrous sodium sulfate and concentrated. To the resulting residue was added hot methanol to crystallize and then cooled. The resulting precipitate was collected by filtration, added to the mixture of concentrated hydrochloric acid-methanol (1:1, 18 ml) and stirred at room temperature for an hour. The reacting mixture was neutralized with concentrated aqueous ammonia and the resulting precipitate was collected by filtration, washed with ice-water sufficiently and recrystallized from dichloromethane-methanol (1:1) to give the title compound (0.41 g) as colorless prisms, mp 232°–234° C. (decompd.).

Analysis (%) for $C_{17}H_{19}F_2N_3O_3 \cdot \frac{1}{2}H_2O$, Calcd. (Found): C, 56.66 (56.99); H, 5.59 (5.45); N, 11.66 (11.76).

EXAMPLE 23

7-(cis-3-Amino-4-methyl-1-pyrrolidinyl)-8-chloro-1-ethyl-6-fluoro-1,4-dihydro-4-oxo-3-quinolinecarboxylic acid A mixture of 8-chloro-1-ethyl-6,7-difluoro-1,4-dihydro-4-oxo-3-quinolinecarboxylic acid (0.25 g), cis-3-t-butoxycarbonylamino-4-methylpyrrolidine (0.21 g), DBU (0.15 g) and anhydrous acetonitrile (4 ml) was refluxed for 2.5 hours. Then, the reacting mixture was treated as described in example 22 to give the title compound (0.1 g) as white powder, mp 222°–224° C. (decompd.).

Analysis (%) for $C_{17}H_{19}ClFN_3O_3.\frac{1}{2}H_2O$, Calcd. (Found): C, 54.62 (54.58); H, 5.30 (5.12); N, 11.24 (11.26).

EXAMPLE 24

7-(cis-3-t-Butoxycarbonylamino-4-methyl-1-pyrrolidinyl)-6,8-difluoro-1-(2-fluoroethyl)-1,4-dihydro-4-oxo-3-quinolinecarboxylic acid A mixture of 6,7,8-trifluoro-1-(2-fluoroethyl)-1,4-dihydro-4-oxo-3-quinolinecarboxylic acid (0.5 g), anhydrous acetonitrile (5 ml), cis-3-t-butoxycarbonylamino-4-methylpyrrolidine (0.5 g) and DBU (0.27 g) was refluxed for an hour and then concentrated. The resulting residue was dissolved in chloroform and the solution was washed with 10% aqueous citric acid solution. After concentration of the chloroform layer, the resulting precipitate was triturated in water, and collected by filtration and washed with water, methanol and ether successively to give the title compound (0.51 g) as white powder, mp 217°–219° C.

Analysis (%) for $C_{22}H_{26}F_3N_3O_5$, Calcd. (Found): C, 56.29 (56.16); H, 5.58 (5.56); N, 8.95 (8.93).

EXAMPLE 25

7-(cis-b 3-Amino-4-methyl-1-pyrrolidinyl)-6,8-difluoro-1-(2-fluoroethyl)-1,4-dihydro-4-oxo-3-quinolinecarboxylic acid A mixture of 7-(cis-3-t-butoxycarbonylamino-4-methyl-1-pyrrolidinyl)-6,8-difluoro-1-(2-fluoroethyl)-1,4-dihydro-4-oxo-3-quinolinecarboxylic acid (0.45 g) in methanol (5 ml) and concentrated hydrochloric acid (5 ml) was stirred at room temperature for 30 minutes. The reacting mixture was neutralized with concentrated aqueous ammonia and then cooled. The resulting precipitate was collected by filtration and washed with water, methanol and ether successively to give the title compound (0.17 g) as pale yellow powder, mp 240°–243° C. (decompd.).

Analysis (%) for $C_{17}H_{18}F_3N_3O_3.3/2H_2O$, Calcd. (Found): C, 51.52 (51.84); H, 5.34 (5.19); N, 10.60 (10.60).

EXAMPLE 26

7-(cis-3-t-Butoxycarbonylamino-4-methyl-1-pyrrolidinyl)-8-chloro-6-fluoro-1-(2-fluoroethyl)-1,4-dihydro-4-oxo-3-quinolinecarboxylic acid A mixture of 8-chloro-6,7-dihydro-1-(2-fluoroethyl)-1,4-dihydro-4-oxo-3-quinolinecarboxylic acid (0.15 g), anhydrous acetonitrile (2 ml), cis-3-t-butoxycarbonylamino-4-methylpyrrolidine (0.15 g) and DBU (0.08 g) was refluxed for an hour and then concentrated. The resulting residue was dissolved in chloroform and the solution was washed with 10% aqueous citric acid solution, saturated aqueous sodium chloride solution successively, dried over anhydrous sodium sulfate and then concentrated. The resulting precipitate was triturated in methanol, collected by filtration and washed with ether to give the title compound (0.17 g) as white powder, mp 229°–231° C. (decompd.).

Analysis (%) for $C_{22}H_{26}ClF_2N_3O_5$, Calcd. (Found): C, 54.38 (54.54); H, 5.39 (5.41); N, 8.65 (8.62).

EXAMPLE 27

7-(cis-3-Amino-4-methyl-1-pyrrolidinyl)-8-chloro-6-fluoro-1-(2-fluoroethyl)-1,4-dihydro-4-oxo-3-quinolinecarboxylic acid A mixture of 7-(cis-3-t-butoxycarbonylamino-4-methyl-1-pyrrolidinyl)-8-chloro-6-fluoro-1-(2-fluoroethyl)-1,4-dihydro-4-oxo-3-quinolinecarboxylic acid (0.13 g) in methanol (1.5 ml) and concentrated hydrochloric acid (1.5 ml) was stirred at room temperature for 30 minutes. The reacting mixture was neutralized with concentrated aqueous ammonia and then cooled. The resulting precipitate was collected by filtration and washed with water, methanol and ether successively to give the title compound (0.05 g) as pale yellow powder, mp 234°–236° C. (decompd.).

Analysis (%) for $C_{17}H_{18}ClF_2N_3O_3.\frac{1}{2}H_2O$, Calcd. (Found): C, 51.72 (51.43); H, 4.85 (5.02); N, 10.64 (10.69).

EXAMPLE 28

10-(cis-3-t-Butoxycarbonylamino-4-methyl-1-pyrrolidinyl)-9-fluoro-2,3-dihydro-3-methyl-7-oxo-7H-pyrido[1,2,3-de][1,4]benzoxazine-6-carboxylic acid A mixture of 9,10-difluoro-2,3-dihydro-3-methyl-7-oxo-7H-pyrido[1,2,3-de][1,4]benzoxazine-6-carboxylic acid (0.5 g), anhydrous dimethyl sulfoxide (10 ml) and cis-3-t-butoxycarbonylamino-4-methylpyrrolidine (0.54 g) was stirred for 2 hours at 90°–100° C. and then concentrated. To the residue was added methanol and the resulting precipitate was collected by filtration and then washed with cold methanol to give the title compound (0.58 g) as yellowish powder, mp 219°–220° C.

Analysis (%) for $C_{23}H_{28}FN_3O_6.H_2O$, Calcd. (Found): C, 57.61 (57.79); H, 6.31 (6.11); N, 8.76 (8.68).

EXAMPLE 29

10-(cis-3-Amino-4-methyl-1-pyrrolidinyl)-9-fluoro-2,3-dihydro-3-methyl-7-oxo-7H-pyrido[1,2,3-de][1,4]benzoxazine-6-carboxylic acid hydrochloride A mixture of 10-(cis-3-t-butoxycarbonylamino-4-methyl-1-pyrrolidinyl)-9-fluoro-2,3-dihydro-3-methyl-7-oxo-7H-pyrido[1,2,3-de][1,4]benzoxazine-6-carboxylic acid (0.55 g) in ethanol (8 ml) and ethanolic hydrochloride solution (10 ml) was stirred for 2 hours at room temperature and then concentrated. To the resulting residue was added ethanol and the resulting precipitate was collected by filtration and then washed with hot ethanol to give the title compound (0.5 g) as yellowish powder, mp 298° C. (decompd.)

Analysis (%) for $C_{18}H_{20}FN_3O_4.HCl$, Calcd. (Found): C, 54.34 (54.06); H, 5.32 (5.43); N, 10.56 (10.41).

EXAMPLE 30

(3S)-10-(cis-3-t-Butoxycarbonylamino-4-methyl-1-pyrrolidinyl)-9-fluoro-2,3-dihydro-3-methyl-7-oxo-7H-pyrido[1,2,3-de][1,4]benzoxazine-6-carboxylic acid A mixture of (3S)-9,10-difluoro-2,3-dihydro-3-methyl-7-oxo-7H-pyrido[1,2,3-de][1,4]benzoxazine-6-carboxylic acid (0.5 g), anhydrous dimethyl sulfoxide (10 ml) and cis-3-t-butoxycarbonylamino-4-methylpyrrolidine (0.54 g) was stirred for 2 hours at 90°–100° C. and then concentrated. The resulting residue was dissolved in chloroform and the solution was washed with 10% aqueous citric acid solution further washed with saturated aqueous sodium chloride solution, dried over anhydrous sodium sulfate and concentrated. The resulting precipitate was triturated in methanol and collected by filtration to give the title compound (0.67 g) as yellowish powder, mp 206°–207° C.

Analysis (%) for $C_{23}H_{28}FN_3O_6 \cdot \frac{3}{4}H_2O$, Calcd. (Found): C, 58.15 (57.85); H, 6.26 (6.25); N, 8.85 (8.75).

EXAMPLE 31

(3S)-10-(cis-3-Amino-4-methyl-1-pyrrolidinyl)-9-fluoro-2,3-dihydro-3-methyl-7-oxo-7H-pyrido[1,2,3-de][1,4]benzoxazine-6-carboxylic acid hydrochloride A mixture of (3S)-10-(cis-3-t-butoxycarbonylamino-4-methyl-1-pyrrolidinyl)-9-fluoro-2,3-dihydro-3-methyl-7-oxo-7H-pyrido[1,2,3-de][1,4]benzoxazine-6-carboxylic acid (0.6 g) in ethanol (8 ml) and ethanolic hydrochloride solution (10 ml) was stirred for 1.5 hours at room temperature and then concentrated. To the residue was added ethanol and the resulting precipitate was collected by filtration to give the title compound (0.44 g) as yellowish powder, mp 285° C. (decompd.).

Analysis (%) for $C_{18}H_{20}FN_3O_4 \cdot HCl \cdot 5/4H_2O$, Calcd. (Found): C, 51.43 (51.59); H, 5.64 (5.51); N, 10.00 (10.02).

EXAMPLE 32

7-(trans-3-Amino-4-methyl-1-pyrrolidinyl)-8-bromo-1-cyclopropyl-6-fluoro-1,4-dihydro-4-oxo-3-quinolinecarboxylic acid A mixture of 8-bromo-1-cyclopropyl-6,7-difluoro-1,4-dihydro-4-oxo-3-quinolinecarboxylic acid (0.11 g), trans-3-t-butoxycarbonylamino-4-methylpyrrolidine (0.082 g), DBU (0.054 g) and anhydrous acetonitrile (5 ml) was refluxed for 1.5 hours and then concentrated. The resulting residue was dissolved in chloroform (50 ml) and washed with 10% aqueous citric acid solution and water successively. The organic layer was concentrated under reduced pressure and to the oily residue was added methanol to crystallize. The resulting precipitate was collected by filtration, washed with chilled methanol and this was added to concentrated hydrochloric acid-methanol (1:1, 2 ml) and stirred for an hour at room temperature. The reacting mixture was neutralized with concentrated aqueous ammonia, concentrated under reduced pressure and the resulting residue was purified by silica gel column chromatography (chloroform:methanol:concentrated aqueous ammonia=20:6:1) and then recrystallized from dichloromethanemethanol (1:1) to give the title compound (0.04 g) as pale yellow powder, mp 186°–190° C. (decompd.).

Analysis (%) for $C_{18}H_{19}BrFN_3O_3$, Calcd. (Found): C, 50.96 (50.91); H, 4.51 (4.60); N, 9.90 (9.72).

EXAMPLE 33

7-(cis-3-Amino-4-methyl-1-pyrrolidinyl)-1-cyclopropyl-6-fluoro-1,4-dihydro-4-oxo-3-quinolinecarboxylic acid A mixture of 7-chloro-1-cyclopropyl-6-fluoro-1,4-dihydro-4-oxo-3-quinolinecarboxylic acid (0.7 g), cis-3-t-butoxycarbonylamino-4-methylpyrrolidine (0.62 g), DBU (0.43 g) and anhydrous acetonitrile (30 ml) was refluxed for 52 hours. After cooling, the resulting precipitate was collected by filtration, washed with chilled acetonitrile and this was added to concentrated hydrochloric acid-methanol (1:1, 5 ml) and stirred for 40 minutes at elevated temperature. The reacting mixture was collected by filtration, washed with chilled water sufficiently and recrystallized from chloroform-methanol-concentrated aqueous ammonia (10:10:3) to give the title compound (0.076 g) as pale yellow prisms, mp 268°–270° C. (decompd.).

Analysis (%) for $C_{18}H_{20}FN_3O_3 \cdot \frac{3}{8}H_2O$, Calcd. (Found): C, 60.49 (60.50); H, 6.02 (6.05); N, 11.76 (11.61).

EXAMPLE 34

7-(cis-3-Amino-4-methyl-1-pyrrolidinyl)-1-ethyl-6-fluoro-1,4-dihydro-4-oxo-3-quinolinecarboxylic acid A mixture of 7-chloro-1-ethyl-6-fluoro-1,4-dihydro-4-oxo-3-quinolinecarboxylic acid (1.0 g), cis-3-t-butoxycarbonylamino-4-methylpyrrolidine (0.89 g), DBU (0.62 g) and anhydrous acetonitrile (30 ml) was refluxed for 27 hours. Then, the reacting mixture was treated as described in example 33 and recrystallized from chloroform-methanol-concentrated aqueous ammonia (20:20:1) to give the title compound (0.008 g) as white powder, mp 300~° C. (decompd.).

Mass (m/e): 333 (M+), 334 (M++1).

Next, we evaluted antibacterial activity of present invented compounds in comparison with that of ciprofloxacin (CPFX), which is considered to be the most excellent compound in the prior arts.

EXPERIMENT 1

Antibacterial Spectrum

Minimal inhibitory concentrations (MICs) were determined in accordance with the method recommended by Japan Society of Chemotherapy. The results were shown in Table 1.

TABLE 1

In vitro antibacterial activity (standard strains)

| Organism ($10^6$ cells/ml) | Gram | MIC (μg/ml) | | | | | | | | | |
|---|---|---|---|---|---|---|---|---|---|---|---|
| | | Exp. 1 | Exp. 2 | Exp. 7 | Exp. 11 | Exp. 12 | Exp. 13 | Exp. 14 | Exp. 15 | Exp. 16 | Exp. 17 |
| *Bacillus subtilis* PCI 219 | + | 0.0125 | 0.0125 | 0.0125 | 0.025 | 0.0125 | 0.025 | 0.0125 | 0.025 | 0.0125 | 0.0125 |
| *Staphylococcus aureus* 209 P | + | 0.0125 | 0.025 | 0.025 | 0.05 | 0.05 | 0.05 | 0.0125 | 0.05 | 0.05 | 0.025 |
| *S. aureus* Smith | + | 0.0125 | 0.025 | 0.05 | 0.05 | 0.05 | 0.05 | 0.0125 | 0.05 | 0.025 | 0.025 |
| *S. aureus* IID 670 (Terajima) | + | 0.025 | 0.025 | 0.05 | 0.10 | 0.0125 | 0.05 | 0.0125 | 0.05 | 0.05 | 0.05 |
| *S. epidermidis* IID 866 | + | 0.0125 | 0.025 | 0.05 | 0.10 | 0.05 | 0.05 | 0.0125 | 0.05 | 0.05 | 0.05 |
| *Streptococcus pyogenes* (S-8) | + | 0.0125 | 0.05 | 0.10 | — | 0.05 | 0.10 | 0.05 | 0.10 | 0.10 | — |
| *S. pyogenes* IID 692 | + | 0.025 | 0.05 | 0.10 | — | 0.05 | 0.20 | 0.05 | 0.10 | 0.10 | — |
| *S. pneumoniae* IID 552 | + | 0.0125 | 0.05 | 0.10 | — | 0.05 | 0.10 | 0.05 | 0.10 | 0.10 | — |
| *E. faecalis* IID 682 | + | 0.05 | 0.10 | 0.10 | — | 0.05 | 0.20 | 0.05 | 0.10 | 0.10 | — |
| *Escherichia coli* NIHJ JC-2 | — | 0.025 | 0.025 | 0.0063 | 0.0125 | 0.05 | 0.05 | 0.025 | 0.05 | 0.0063 | 0.0063 |
| *E. coli* ATCC 10536 | — | 0.025 | 0.025 | 0.0125 | 0.025 | 0.05 | 0.05 | 0.025 | 0.05 | 0.0125 | 0.0063 |
| *E. coli* ML 4707 | — | 0.025 | 0.025 | 0.0125 | 0.0125 | 0.025 | 0.05 | 0.05 | 0.05 | 0.0063 | 0.0063 |
| *Proteus vulgaris* IFO 3167 | — | 0.05 | 0.05 | 0.0125 | 0.025 | 0.05 | 0.05 | 0.05 | 0.10 | 0.0125 | 0.0125 |

TABLE 1-continued

In vitro antibacterial activity (standard strains)

| Organism | Gram | | | | | | | | | | |
|---|---|---|---|---|---|---|---|---|---|---|---|
| P. mirabilis IID 994 | — | 0.05 | 0.05 | 0.025 | 0.05 | 0.20 | 0.20 | 0.10 | 0.10 | 0.025 | 0.025 |
| Morganella morganii IID 602 | — | 0.10 | 0.10 | 0.05 | 0.05 | 0.20 | 0.20 | 0.20 | 0.20 | 0.05 | 0.05 |
| Klebsiella pneumoniae KY(GN)6445 | — | 0.05 | 0.05 | 0.0125 | 0.025 | 0.05 | 0.05 | 0.05 | 0.05 | 0.025 | 0.0125 |
| K. pneumoniae 1-220S | — | 0.05 | 0.05 | 0.05 | 0.05 | 0.10 | 0.20 | 0.20 | 0.20 | 0.05 | 0.0125 |
| Enterobacter cloacae IID 977 | — | 0.05 | 0.05 | 0.05 | 0.05 | 0.20 | 0.20 | 0.20 | 0.20 | 0.05 | 0.05 |
| Citrobacter freundii IID 976 | — | 0.05 | 0.05 | 0.025 | 0.05 | 0.05 | 0.05 | 0.10 | 0.10 | 0.025 | 0.0125 |
| Serratia marcescens IID 618 | — | 0.10 | 0.10 | 0.05 | 0.05 | 0.20 | 0.20 | 0.20 | 0.20 | 0.05 | 0.05 |
| Shigella sonnei IID 969 | — | 0.025 | 0.025 | 0.0063 | 0.025 | 0.025 | 0.05 | 0.025 | 0.05 | 0.0063 | 0.0063 |
| Salmonella enteritidis IID 604 | — | 0.05 | 0.05 | 0.025 | 0.05 | 0.10 | 0.10 | 0.20 | 0.20 | 0.025 | 0.025 |
| Pseudomonas aeruginosa V-1 | — | 0.10 | 0.10 | 0.20 | 0.39 | 0.39 | 0.39 | 0.78 | 0.78 | 0.10 | 0.10 |
| P. aeruginosa IFO 12689 | — | 0.78 | 0.78 | 0.39 | 0.39 | 1.56 | 3.13 | 3.13 | 3.13 | 0.39 | 0.39 |
| P. aeruginosa IID 1210 | — | 0.78 | 0.78 | 0.39 | 0.39 | 1.56 | 1.56 | 3.13 | 3.13 | 0.39 | 0.39 |
| P. cepacia GIFU 518 | — | 0.39 | 0.39 | 0.20 | 0.39 | 0.78 | 0.78 | 0.78 | 0.78 | 0.39 | 0.20 |
| P. maltophilia GIFU 2491 | — | 0.10 | 0.20 | 0.05 | 0.10 | 0.20 | 0.39 | 0.39 | 0.39 | 0.05 | 0.05 |
| Yersinia enterocolitica IID 981 | — | 0.05 | 0.05 | 0.025 | 0.05 | 0.10 | 0.10 | 0.20 | 0.20 | 0.05 | 0.025 |
| Acinetobacter anitratus IID 876 | — | 0.05 | 0.05 | 0.025 | 0.05 | 0.20 | 0.10 | 0.10 | 0.10 | 0.025 | 0.025 |
| Alcaligenes faecalis 0114002 | — | 0.20 | 0.20 | 0.10 | 0.20 | 0.39 | 0.78 | 0.78 | 0.78 | 0.10 | 0.05 |
| Bacteroides fragilis GM 7000 | — | ≦0.10 | 0.78 | 0.10 | 0.78 | 0.20 | 0.78 | 0.10 | 0.78 | 0.05 | 0.05 |
| B. fragilis 0558 | — | ≦0.05 | 0.39 | 0.05 | 0.39 | 0.10 | 0.78 | ≦0.05 | 0.39 | 0.05 | 0.05 |
| B. fragilis 25285 | — | ≦0.05 | 0.39 | 0.05 | 0.39 | 0.10 | 0.78 | 0.05 | 0.39 | 0.05 | 0.05 |
| B. distasonis 8503 | — | 0.39 | 3.13 | 0.39 | 0.78 | 0.39 | 3.13 | 0.39 | 3.13 | 0.20 | 0.10 |
| B. thetaiotaomicron (0661) | — | 0.10 | 0.78 | 0.20 | 0.78 | 0.39 | 3.13 | 0.20 | 1.56 | 0.10 | 0.10 |
| B. vulgatus KYA 29327 | — | 0.10 | 0.78 | 0.10 | 0.39 | 0.20 | 1.56 | ≦0.05 | 0.78 | 0.05 | 0.05 |
| Fusobacterium mortiferum 4249 | — | ≦0.05 | 0.39 | 0.20 | 0.39 | 0.20 | 0.39 | 0.20 | 0.39 | 0.10 | 0.10 |
| F. necrophorum S-45 | — | 0.10 | 0.39 | 0.20 | 0.39 | 0.20 | 0.39 | 0.10 | 0.39 | 0.05 | 0.05 |
| F. varium KYA 8501 | — | 0.39 | 0.78 | 0.78 | 1.56 | 0.78 | 1.56 | 1.56 | 1.56 | 0.78 | 0.78 |
| Eubacterium lentum GAI 5242 | + | 0.20 | 0.78 | 0.10 | 0.39 | 0.20 | 0.78 | 0.20 | 0.39 | 0.05 | 0.05 |
| E. limosum KYA 8486 | + | 0.39 | 1.56 | 0.20 | 0.78 | 0.39 | 1.56 | 0.78 | 1.56 | — | — |
| Propionibacterium acens 11828 | + | 0.20 | 0.39 | 0.78 | 3.13 | 0.78 | 1.56 | 1.56 | 3.13 | 0.78 | 0.78 |
| Peptococcus magnus KY 017 | + | ≦0.05 | 0.20 | 0.05 | 0.20 | 0.05 | ≦0.05 | ≦0.05 | ≦0.05 | 0.05 | 0.05 |
| Clostridium difficile I-E | + | — | — | — | — | 0.20 | 0.78 | 0.10 | 0.78 | 0.39 | 0.39 |
| C. perfringens KYA 13123 | + | ≦0.05 | 0.20 | 0.10 | 0.39 | 0.10 | 0.20 | ≦0.05 | 0.10 | 0.05 | 0.05 |
| C. ramosum | + | 0.20 | 0.78 | 0.78 | 1.56 | 0.39 | 0.78 | 0.20 | 0.78 | 0.39 | 0.39 |
| Peptostreptococcus anaerobius KYA 27337 | + | ≦0.05 | 0.10 | 0.20 | 0.39 | 0.05 | 0.20 | ≦0.05 | 0.20 | 0.10 | 0.10 |
| Pst. micros UPI 5464-1 | + | 0.39 | 0.39 | 0.10 | 0.39 | 0.39 | 0.78 | 0.39 | 0.78 | 0.10 | 0.05 |
| Veillonella parvula KYA 10790 | — | 0.10 | 0.39 | 0.10 | 0.39 | 0.39 | 0.78 | 0.39 | 0.78 | 0.10 | 0.05 |

| Organism ($10^6$ cells/ml) | Gram | MIC (μg/ml) | | | | | | | | | |
|---|---|---|---|---|---|---|---|---|---|---|---|
| | | Exp. 18 | Exp. 20 | Exp. 21 | Exp. 22 | Exp. 23 | Exp. 25 | Exp. 27 | Exp. 29 | Exp. 31 | Exp. 32 |
| Bacillus subtilis PCI 219 | + | 0.025 | 0.025 | 0.0125 | 0.05 | 0.05 | 0.10 | 0.10 | 0.05 | 0.05 | 0.0125 |
| Staphylococcus aureus 209 P | + | 0.05 | 0.05 | 0.025 | 0.10 | 0.10 | 0.20 | 0.20 | 0.20 | 0.20 | 0.025 |
| S. aureus Smith | + | 0.05 | 0.05 | 0.025 | 0.20 | 0.20 | 0.39 | 0.20 | 0.20 | 0.20 | 0.025 |
| S. aureus IID 670 (Terajima) | + | 0.20 | 0.05 | 0.05 | 0.20 | 0.20 | 0.39 | 0.39 | 0.39 | 0.20 | 0.05 |
| S. epidermidis IID 866 | + | 0.05 | 0.05 | 0.05 | 0.20 | 0.20 | 0.39 | 0.20 | 0.20 | 0.20 | 0.05 |
| Streptococcus pyogenes (S-8) | + | 0.05 | 0.20 | 0.10 | 0.78 | 0.78 | 0.78 | 0.78 | 0.39 | 0.20 | 0.10 |
| S. pyogenes IID 692 | + | 0.10 | 0.39 | 0.20 | 0.78 | 0.78 | 0.78 | 0.78 | 0.39 | 0.20 | 0.20 |
| S. pneumoniae IID 552 | + | 0.05 | 0.20 | 0.20 | 0.78 | 0.78 | 0.78 | 0.78 | 0.39 | 0.20 | 0.10 |
| E. faecalis IID 682 | + | 0.10 | 0.20 | 0.20 | 0.78 | 0.78 | 0.78 | 0.78 | 0.39 | 0.20 | 0.20 |
| Escherichia coli NIHJ JC-2 | — | 0.0063 | 0.0125 | 0.0063 | 0.05 | 0.025 | 0.05 | 0.05 | 0.025 | 0.025 | 0.0063 |
| E. coli ATCC 10536 | — | 0.05 | 0.025 | 0.0125 | 0.05 | 0.05 | 0.05 | 0.05 | 0.05 | 0.025 | 0.0125 |
| E. coli ML 4707 | — | 0.0063 | 0.025 | 0.0125 | 0.05 | 0.05 | 0.05 | 0.05 | 0.05 | 0.025 | 0.0125 |
| Proteus vulgaris IFO 3167 | — | 0.0125 | 0.025 | 0.0125 | 0.05 | 0.05 | 0.05 | 0.05 | 0.05 | 0.10 | 0.0125 |
| P. mirabilis IID 994 | — | 0.025 | 0.05 | 0.025 | 0.10 | 0.05 | 0.10 | 0.10 | 0.10 | 0.10 | 0.05 |
| Morganella morganii IID 602 | — | 0.05 | 0.05 | 0.05 | 0.20 | 0.10 | 0.10 | 0.10 | 0.10 | 0.20 | 0.05 |
| Klebsiella pneumoniae KY(GN)6445 | — | 0.0125 | 0.025 | 0.0125 | 0.05 | 0.05 | 0.10 | 0.10 | 0.05 | 0.05 | 0.025 |
| K. pneumoniae 1-220S | — | 0.025 | 0.05 | 0.05 | 0.10 | 0.10 | 0.20 | 0.20 | 0.20 | 0.10 | 0.05 |
| Enterobacter cloacae IID 977 | — | 0.05 | 0.05 | 0.025 | 0.10 | 0.10 | 0.10 | 0.10 | 0.20 | 0.10 | 0.05 |
| Citrobacter freundii IID 976 | — | 0.0125 | 0.025 | 0.025 | 0.05 | 0.05 | 0.05 | 0.05 | 0.10 | 0.05 | 0.025 |
| Serratia marcescens IID 618 | — | 0.05 | 0.05 | 0.025 | 0.10 | 0.05 | 0.10 | 0.10 | 0.10 | 0.10 | 0.05 |
| Shigella sonnei IID 969 | — | 0.0125 | 0.0125 | 0.0063 | 0.10 | 0.05 | 0.78 | 0.78 | 0.05 | 0.05 | 0.0063 |
| Salmonella enteritidis IID 604 | — | 0.025 | 0.05 | 0.025 | 0.10 | 0.10 | 0.10 | 0.10 | 0.10 | 0.10 | 0.05 |
| Pseudomonas aeruginosa V-1 | — | 0.10 | 0.20 | 0.39 | 0.39 | 0.39 | 0.78 | 0.39 | 0.39 | 0.39 | 0.20 |
| P. aeruginosa IFO 12689 | — | 0.39 | 0.39 | 0.78 | 1.56 | 1.56 | 1.56 | 3.13 | 1.56 | 0.78 | 0.39 |
| P. aeruginosa IID 1210 | — | 0.78 | 0.78 | 1.56 | 6.25 | 6.25 | 6.25 | 6.25 | 6.25 | 3.13 | 0.78 |
| P. cepacia GIFU 518 | — | 0.10 | 0.39 | 0.39 | 0.78 | 0.78 | 1.56 | 0.78 | 1.56 | 1.56 | — |
| P. maltophilia GIFU 2491 | — | 0.05 | 0.39 | 0.05 | 0.78 | 0.39 | 1.56 | 1.56 | 1.56 | 0.78 | 0.05 |
| Yersinia enterocolitica IID 981 | — | 0.05 | 0.05 | 0.025 | 0.10 | 0.05 | 0.10 | 0.10 | 0.20 | 0.10 | 0.025 |
| Acinetobacter anitratus IID 876 | — | 0.025 | 0.05 | 0.025 | 0.39 | 0.39 | 1.56 | 1.56 | 1.56 | 1.56 | 0.025 |
| Alcaligenes faecalis 0114002 | — | 0.10 | 0.39 | 0.20 | 1.56 | 1.56 | 0.78 | 0.78 | 1.56 | 0.39 | 0.10 |
| Bacteroides fragilis GM 7000 | — | 0.20 | 0.39 | 0.10 | 3.13 | 0.78 | 6.25 | 1.56 | 3.13 | 1.56 | 0.10 |
| B. fragilis 0558 | — | 0.20 | 0.39 | 0.05 | 1.56 | 0.78 | 3.13 | 1.56 | 1.56 | 0.78 | 0.05 |
| B. fragilis 25285 | — | 0.20 | 0.39 | 0.05 | 1.56 | 0.78 | 3.13 | 1.56 | 1.56 | 0.78 | 0.10 |
| B. distasonis 8503 | — | 0.39 | 0.78 | 0.39 | 3.13 | 3.13 | 6.25 | 6.25 | — | — | 0.20 |
| B. thetaiotaomicron (0661) | — | 0.39 | 0.78 | 0.20 | 3.13 | 1.56 | 6.25 | 3.13 | 6.25 | 3.13 | 0.20 |
| B. vulgatus KYA 29327 | — | 0.39 | 0.39 | 0.10 | 3.13 | 1.56 | 6.25 | 3.13 | 6.25 | 3.13 | 0.20 |
| Fusobacterium mortiferum 4249 | — | 0.20 | 0.39 | 0.20 | 1.56 | 1.56 | 3.13 | 1.56 | 0.78 | 0.39 | 0.20 |
| F. necrophorum S-45 | — | 0.20 | 0.39 | 0.20 | 3.13 | 1.56 | 3.13 | 1.56 | 0.78 | 0.39 | 0.10 |
| F. varium KYA 8501 | — | 1.56 | 1.56 | 0.78 | 6.25 | 6.25 | 6.25 | 6.25 | 6.25 | 3.13 | 0.78 |
| Eubacterium lentum GAI 5242 | + | 0.10 | 0.20 | 0.05 | 1.56 | 1.56 | 1.56 | 0.78 | 0.78 | 0.39 | 0.10 |

TABLE 1-continued

In vitro antibacterial activity (standard strains)

| | | | | | | | | | | | |
|---|---|---|---|---|---|---|---|---|---|---|---|
| E. limosum KYA 8486 | + | — | — | — | 6.25 | 6.25 | 6.25 | 6.25 | 6.25 | 3.13 | 0.10 |
| Propionibacterium acens 11828 | + | 1.56 | 3.13 | 1.56 | 25 | 12.5 | 25 | 12.5 | 12.5 | 6.25 | 1.56 |
| Peptococcus magnus KY 017 | + | 0.05 | 0.20 | 0.05 | 1.56 | 0.78 | 1.56 | 0.78 | 0.78 | 0.20 | 0.05 |
| Clostridium difficile I-E | + | 1.56 | 1.56 | 0.39 | 6.25 | 6.25 | 6.25 | 6.25 | 6.25 | 3.13 | 0.78 |
| C. perfringens KYA 13123 | + | 0.10 | 0.20 | 0.10 | 0.78 | 0.78 | 0.78 | 0.39 | 0.39 | 0.20 | 0.20 |
| C. ramosum | + | 0.78 | 1.56 | 0.78 | 6.25 | 6.25 | 25 | 25 | 12.5 | 6.25 | 0.78 |
| Peptostreptococcus anaerobius KYA 27337 | + | 0.20 | 0.39 | 0.20 | 3.13 | 1.56 | 3.13 | 1.56 | 1.56 | 0.39 | 0.20 |
| Pst. micros UPI 5464-1 | + | 0.10 | 0.20 | 0.10 | 0.78 | 0.78 | 0.78 | 0.39 | 0.39 | 0.20 | 0.10 |
| Veillonella parvula KYA 10790 | — | 0.10 | 0.20 | 0.10 | 0.78 | 0.78 | 0.78 | 0.39 | 0.39 | 0.20 | 0.10 |

| Organism ($10^6$ cells/ml) | Gram | MIC (µg/ml) | | |
|---|---|---|---|---|
| | | Exp. 33 | CPFX | NFLX |
| Bacillus subtilis PCI 219 | + | 0.05 | 0.05 | 0.10 |
| Staphylococcus aureus 209 P | + | 0.05 | 0.39 | 0.78 |
| S. aureus Smith | + | 0.10 | 0.39 | 0.78 |
| S. aureus IID 670 (Terajima) | + | 0.10 | 0.39 | 1.56 |
| S. epidermidis IID 866 | + | 0.10 | 0.39 | 0.78 |
| Streptococcus pyogenes (S-8) | + | 0.78 | 0.39 | 1.56 |
| S. pyogenes IID 692 | + | 0.39 | 0.78 | 3.13 |
| S. pneumoniae IID 552 | + | 0.39 | 1.56 | 3.13 |
| E. faecalis IID 682 | + | 0.39 | 0.78 | 1.56 |
| Escherichia coli NIHJ JC-2 | — | 0.05 | ≦0.0063 | 0.05 |
| E. coli ATCC 10536 | — | 0.05 | 0.0125 | 0.05 |
| E. coli ML 4707 | — | 0.05 | ≦0.0063 | 0.05 |
| Proteus vulgaris IFO 3167 | — | 0.05 | ≦0.0063 | 0.05 |
| P. mirabilis IID 994 | — | 0.05 | 0.0125 | 0.05 |
| Morganella morganii IID 602 | — | 0.05 | 0.05 | 0.05 |
| Klebsiella pneumoniae KY(GN)6445 | — | 0.05 | 0.0125 | 0.05 |
| K. pneumoniae 1-220S | — | 0.05 | 0.05 | 0.10 |
| Enterobacter cloacae IID 977 | — | 0.05 | 0.05 | 0.10 |
| Citrobacter freundii IID 976 | — | 0.05 | ≦0.0063 | 0.05 |
| Serratia marcescens IID 618 | — | 0.05 | 0.39 | 0.05 |
| Shigella sonnei IID 969 | — | 0.05 | ≦0.0063 | 0.05 |
| Salmonella enteritidis IID 604 | — | 0.05 | 0.025 | 0.05 |
| Pseudomonas aeruginosa V-1 | — | 0.20 | 0.20 | 0.39 |
| P. aeruginosa IFO 12689 | — | 0.39 | 0.39 | 0.78 |
| P. aeruginosa IID 1210 | — | 1.56 | 0.78 | 3.13 |
| P. cepacia GIFU 518 | — | — | — | — |
| P. maltophilia GIFU 2491 | — | 0.39 | 0.39 | 6.25 |
| Yersinia enterocolitica IID 981 | — | 0.05 | 0.025 | 0.10 |
| Acinetobacter anitratus IID 876 | — | 0.10 | 0.025 | 1.56 |
| Alcaligenes faecalis 0114002 | — | 0.20 | 0.39 | 1.56 |
| Bacteroides fragilis GM 7000 | — | 1.56 | 3.13 | 25 |
| B. fragilis 0558 | — | 1.56 | 3.13 | 25 |
| B. fragilis 25285 | — | 1.56 | 6.25 | 25 |
| B. distasonis 8503 | — | 6.25 | 6.25 | — |
| B. thetaiotaomicron (0661) | — | 6.25 | 25 | — |
| B. vulgatus KYA 29327 | — | 6.25 | — | — |
| Fusobacterium mortiferum 4249 | — | 1.56 | — | — |
| F. necrophorum S-45 | — | 1.56 | 1.56 | — |
| F. varium KYA 8501 | — | 12.5 | 12.5 | 100 |
| Eubacterium lentum GAI 5242 | + | 0.78 | 0.78 | — |
| E. limosum KYA 8486 | + | 0.20 | — | — |
| Propionibacterium acens 11828 | + | 12.5 | 12.5 | — |
| Peptococcus magnus KY 017 | + | 0.39 | 0.39 | — |
| Clostridium difficile I-E | + | 6.25 | — | 50 |
| C. perfringens KYA 13123 | + | 0.78 | 0.39 | — |
| C. ramosum | + | 6.25 | 6.25 | 50 |
| Peptostreptococcus anaerobius KYA 27337 | + | 1.56 | 1.56 | — |
| Pst. micros UPI 5464-1 | + | 0.39 | 0.20 | — |
| Veillonella parvula KYA 10790 | — | 0.39 | 0.20 | — |

CPFX: ciprofloxacin
NFLX: norfloxacin

EXPERIMENT 2

Therapeutic Efficacy Against Systemic Infections in Mice

In each experiment, five ICR mice were used in each group. Mice were inoculated intraperitoneally with bacterial suspension and the compounds were administered orally with five dosage at one hour after infection.

The number of survivors was determined daily for 3 to 7 days. The 50% effective dose ($ED_{50}$) which protects 50% of animals from death caused by the infection was determined from the relation between dosage and survival rate.

The results were shown in Table 2 to 4.

The protective effectiveness of the present compound was much greater than that of reference compounds.

TABLE 2

| | E. coli ML 4707 | |
|---|---|---|
| | MIC (µg/ml) | $ED_{50}$ (mg/kg) |
| Example 11 | 0.025 | 1.0 |

TABLE 2-continued

| | E. coli ML 4707 | |
| --- | --- | --- |
| | MIC (μg/ml) | ED$_{50}$ (mg/kg) |
| Example 16 | 0.0125 | 1.0 |
| CPFX | 0.0125 | 1.4 |

Challenge dose: 8.5 × 10$^6$ cfu/mouse

TABLE 3

| | MR S. aureus KYB 623 | |
| --- | --- | --- |
| | MIC (μg/ml) | ED$_{50}$ (mg/kg) |
| Example 16 | 0.025 | 3.7 |
| Example 17 | 0.0125 | 2.1 |
| CPFX | 0.39 | 37 |
| | | (+Mucin) |

Challenge dose: 3.1 × 10$^8$ cfu/mouse

TABLE 4

| | S. pneumoniae S-4288 | |
| --- | --- | --- |
| | MIC (μg/ml) | ED$_{50}$ (mg/kg) |
| Example 11 | 0.20 | 20.7 |
| Example 16 | 0.10 | 12.1 |
| CPFX | 1.56 | >100 |

Challenge dose: 4.8 × 10$^6$ cfu/mouse

What is claimed is:

1. A compound of formula (I)

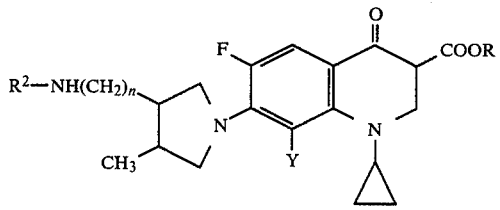

wherein:

R is a hydrogen atom or a lower alkyl group;

Y is a hydrogen atom or a halogen atom;

R$^2$ is a hydrogen atom, a lower alkyl group, an alkoxycarbonyl group, or an acyl group; and n is 0 or 1; or a hydrate or a pharmaceutically acceptable acid addition or alkali salt of said compound of formula (I).

2. The compound of claim 1, wherein said alkyl group is methyl, ethyl or isopropyl.

3. The compound of claim 1, wherein said halogen atom is fluorine, chlorine, bromine or iodine.

4. The compound of claim 1, wherein said alkoxycarbonyl group is methoxycarbonyl, ethoxycarbonyl, t-butoxycarbonyl, or benzyloxycarbonyl, and wherein said acyl group is formyl, acetyl, propionyl, or benzyl.

5. The compound of claim 1, said compound being 7-(3-aminomethyl-4-methyl-1-pyrrolidinyl)-8-chloro-1-cyclopropyl-6-fluoro-1,4-dihydro-4-oxo-3-quinolinecarboxylic acid or 7-(3-aminomethyl-4-methyl-1-pyrrolidinyl)-1-cyclopropyl-6,8-difluoro-1,4-dihydro-4-oxo-3-quinolinecarboxylic acid.

6. The compound of claim 1, said compound being 7-(3-t-butoxycarbonylamino-4-methyl-1-pyrrolidinyl)-8-chloro-1-cyclopropyl-6-fluoro-1,4-dihydro-4-oxo-3-quinolinecarboxylic acid.

7. The compound of claim 1, wherein said compound is 7-(3-amino-4-methyl-1-pyrrolidinyl)-8-chloro-1-cyclopropyl-6-fluoro-1,4-dihydro-4-oxo-3-quinolinecarboxylic acid or 7-[3-(N-acetyl-N-methylamino)-4-methyl-1-pyrrolidinyl]-1-cyclopropyl-6,8-difluoro-1,4-dihydro-4-oxo-3-quinolinecarboxylic acid.

8. The compound of claim 1, said compound being 1-cyclopropyl-6,8-difluoro-1,4-dihydro-7-(3-methylamino-4-methyl-1-pyrrolidinyl)-4-oxo-3-quinolinecarboxylic acid hydrochloride or 7-(3-butoxycarbonylamino-4-methyl-1-pyrrolidinyl)-1-cyclopropyl-6,8-difluoro-1,4-dihydro-4-oxo-3-quinolinecarboxylic acid.

9. The compound of claim 1, said compound being 7-(3-amino-4-methyl-1-pyrrolidinyl)-1-cyclopropyl-6,8-difluoro-1,4,-dihydro-4-oxo-3-quinolinecarboxylic acid hydrochloride or 8-chloro-1-cyclopropyl-6-fluoro-1,4-dihydro-7-(3-methylaminomethyl-4-methyl-1-pyrrolidinyl)-4-oxo-3-quinolinecarboxylic acid.

10. The compound of claim 1, said compound being 1-cyclopropyl-6,8-difluoro-1,4-dihydro-7-(3-methylaminomethyl-4-methyl-1-pyrrolidinyl)-4-oxo-3-quinolinecarboxylic acid or 8-chloro-1-cyclopropyl-7-(3-ethylaminomethyl-4-methyl-1-pyrrolidinyl)-6-fluoro-1,4-dihydro-4-oxo-3-quinolinecarboxylic acid.

11. The compound of claim 1, said compound being 1-cyclopropyl-7-(3-ethylaminomethyl-4-methyl-1-pyrrolidinyl)-6,8-difluoro-1,4-dihydro-4-oxo-3-quinolinecarboxylic acid or 7-(cis-3-amino-4-methyl-1-pyrrolidinyl)-8-chloro-1-cyclopropyl-6-fluoro-1,4-dihydro-4-oxo-3-quinolinecarboxylic acid.

12. The compound of claim 1, said compound being 7-(trans-3-amino-4-methyl-1-pyrrolidinyl)-8-chloro-1-cyclopropyl-6-fluoro-1,4-dihydro-4-oxo-3-quinolinecarboxylic acid or 7-(trans-3-amino-4-methyl-1-pyrrolidinyl)-1-cyclopropyl-6,8-difluoro-1,4-dihydro-4-oxo-3-quinolinecarboxylic acid.

13. The compound of claim 1, said compound being 7-(cis-3-t-butoxycarbonylamino-4-methyl-1-pyrrolidinyl)-1-cyclopropyl-6,8-difluoro-1,4-dihydro-4-oxo-3-quinolinecarboxylic acid or 7-(cis-3-amino-4-methyl-1-pyrrolidinyl)-8-bromo-1-cyclopropyl-6-fluoro-1,4-dihydro-4-oxo-3-quinolinecarboxylic acid.

14. The compound of claim 1, said compound being 7-(trans-3-amino-4-methyl-1-pyrrolidinyl)-8-bromo-1-cyclopropyl-6-fluoro-1,4-dihydro-4-oxo-3-quinolinecarboxylic acid or 7-(cis-3-amino-4-methyl-1-pyrrolidinyl)-1-cyclopropyl-6-fluoro-1,4-dihydro-4-oxo-3-quinoline carboxylic acid.

15. An antibacterial pharmaceutical composition comprising a pharmaceutically effective amount of at least one compound according to claim 1 and an inert pharmaceutically acceptable carrier.

* * * * *